(12) United States Patent
Agarwal et al.

(10) Patent No.: US 10,584,234 B1
(45) Date of Patent: Mar. 10, 2020

(54) ANTIOXIDANT PRECURSORS FOR ELASTOMERIC COMPOSITIONS

(71) Applicant: FIRESTONE INDUSTRIAL PRODUCTS COMPANY, LLC, Nashville, TN (US)

(72) Inventors: Sheel P. Agarwal, Solon, OH (US); William L. Hergenrother, Akron, OH (US)

(73) Assignee: Firestone Industrial Products Company, LLC, Nashville, TN (US)

( * ) Notice: Subject to any disclaimer, the term of this patent is extended or adjusted under 35 U.S.C. 154(b) by 71 days.

(21) Appl. No.: 16/017,361

(22) Filed: Jun. 25, 2018

Related U.S. Application Data

(60) Provisional application No. 62/526,048, filed on Jun. 28, 2017.

(51) Int. Cl.
   *C08L 7/00* (2006.01)
   *C08L 9/00* (2006.01)
   (Continued)

(52) U.S. Cl.
   CPC .............. *C08L 7/00* (2013.01); *C07F 7/1804* (2013.01); *C08L 9/00* (2013.01); *F16F 9/0409* (2013.01);
   (Continued)

(58) Field of Classification Search
   CPC .......... C08L 7/00; C08L 9/00; C08L 2201/08; C08L 2312/00; C07F 7/1804;
   (Continued)

(56) References Cited

U.S. PATENT DOCUMENTS

| 4,105,685 A | * | 8/1978 | Fory | C07F 7/0812 504/164 |
| 4,439,615 A | | 3/1984 | Rosenberger et al. | |

(Continued)

OTHER PUBLICATIONS

Chakraborty, K.B. and Clay, R., Recent developments in polymer stabilization by network-bound AO, Proceedings International Rubber Technology Conference 1988, Malaysian Rubber Board Publication, #8799.

(Continued)

*Primary Examiner* — William K Cheung
(74) *Attorney, Agent, or Firm* — Brian D. McAlhaney; Arthur M. Reginelli

(57) ABSTRACT

An antioxidant precursor compound represented by the formula

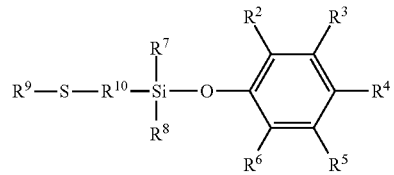

where $R^2$ through $R^6$ are each independently a hydrogen atom or a monovalent organic group, $R^7$ and $R^8$ are each independently a monovalent organic group, $R^9$ is a hydrogen atom or a blocking group, and $R^{10}$ is a covalent bond or a divalent organic group, with the proviso that at least one of $R^2$ and $R^6$ are sterically bulky groups.

15 Claims, 4 Drawing Sheets

(51) Int. Cl.
*C07F 7/18* (2006.01)
*F16F 9/04* (2006.01)
*B60C 1/00* (2006.01)

(52) U.S. Cl.
CPC .......... *B60C 1/0008* (2013.01); *B60C 1/0025* (2013.01); *C08L 2201/08* (2013.01); *C08L 2312/00* (2013.01); *F16F 2224/025* (2013.01)

(58) Field of Classification Search
CPC . F16F 9/0409; F16F 2224/025; B60C 1/0008; B60C 1/0025
USPC .......................................................... 524/262
See application file for complete search history.

(56) References Cited

U.S. PATENT DOCUMENTS

| | | |
|---|---|---|
| 4,739,014 A | 4/1988 | Parks et al. |
| 4,806,447 A | 2/1989 | Parker |
| 4,857,596 A | 8/1989 | MacLeay et al. |
| 4,863,999 A | 9/1989 | MacLeay et al. |
| 4,868,246 A | 9/1989 | MacLeay et al. |
| 5,091,449 A | 2/1992 | Cantillo et al. |
| 6,184,276 B1 | 2/2001 | Ignatz-Hoover |
| 2002/0082334 A1 | 6/2002 | Kobayashi et al. |
| 2002/0156169 A1 | 10/2002 | Kondo et al. |
| 2003/0199619 A1 | 10/2003 | Cruse |
| 2014/0357804 A1 | 12/2014 | Ito et al. |

OTHER PUBLICATIONS

Horvath, J.W., Grimm, D.C. and Stevick, J.A., Improved NBR service performance with polymerization stabilized nitrile rubbers, J. Elastomers and Plastics, Oct. 1975, vol. 7, p. 337.

Sulekha, P.B. and Joseph, R., Preparation and characterisation of novel phenolic antioxidants and its use in natural rubber, J. of Elastomers and Plastics, Jan. 2003, vol. 35.

Al-Mehdawe, M.S. and Stuckey, J.E., Rubber-bound antioxidants; amine antioxidants bound to chloroprene rubber, Rubber Chem & Tech, Mar. 1989, vol. 62, Issue 1.

* cited by examiner

ANTIOXIDANT PRECURSORS FOR ELASTOMERIC COMPOSITIONS

This application claims the benefit of U.S. Provisional Application Ser. No. 62/526,048 filed on Jun. 28, 2017, which is incorporated herein by reference

FIELD OF THE INVENTION

Embodiments of the present invention are directed toward antioxidant precursors and their use in elastomeric compositions.

BACKGROUND OF THE INVENTION

Antioxidants are often employed to protect unsaturated rubber material from oxygen degradation. The poor solubility of some antioxidants may limit the amount of antioxidant that can be introduced into a rubber stock. The effectiveness of the antioxidant may be short-lived if it migrates too quickly to the surface of the material. At the same time, the effectiveness of the antioxidant may be hampered if the antioxidant is not free to migrate throughout the rubber stock.

Because there is an ongoing need to improve the resistance of various rubber goods to degradative effects of oxygen and ozone, there is a desired to better balance the effectiveness of antioxidant behavior.

SUMMARY OF THE INVENTION

Embodiments of the invention provide an antioxidant precursor compound represented by the formula

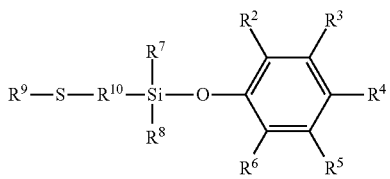

where $R^2$ through $R^6$ are each independently a hydrogen atom or a monovalent organic group, $R^7$ and $R^8$ are each independently a monovalent organic group, $R^9$ is a hydrogen atom or a blocking group, and $R^{10}$ is a covalent bond or a divalent organic group, with the proviso that at least one of $R^2$ and $R^6$ are sterically bulky groups.

Embodiments of the invention provide a vulcanizable composition of matter comprising: (i) a vulcanizable elastomer; (ii) a curative for the vulcanizable elastomer; and (iii) an antioxidant precursor compound defined by the formula

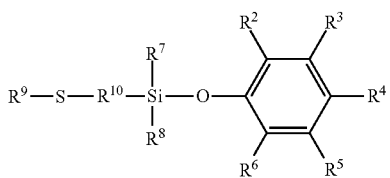

or a polymer-bound antioxidant precursor of the formula

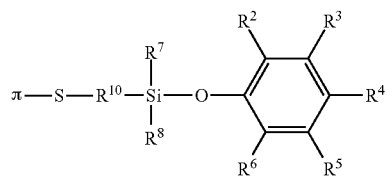

where $R^2$ through $R^6$ are each independently a hydrogen atom or a monovalent organic group, $R^7$ and $R^8$ are each independently a monovalent organic group, $R^{10}$ is a covalent bond or a divalent organic group, with the proviso that at least one of $R^2$ and $R^6$ are sterically bulky groups, $R^9$ is a hydrogen atom or a blocking group, and π is a polymer chain.

Yet other embodiments provide a cured rubber article comprising: a cross-linked polymer network defined by the formula

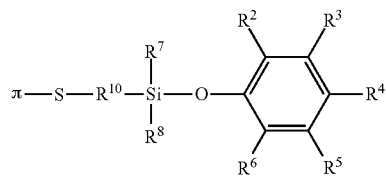

where $R^2$ through $R^6$ are each independently a hydrogen atom or a monovalent organic group, $R^7$ and $R^8$ are each independently a monovalent organic group, $R^{10}$ is a covalent bond or a divalent organic group, with the proviso that at least one of $R^2$ and $R^6$ are sterically bulky groups, and π is a polymer chain or a cross-linked polymer network.

DETAILED DESCRIPTION OF ILLUSTRATIVE EMBODIMENTS

Figure 1:
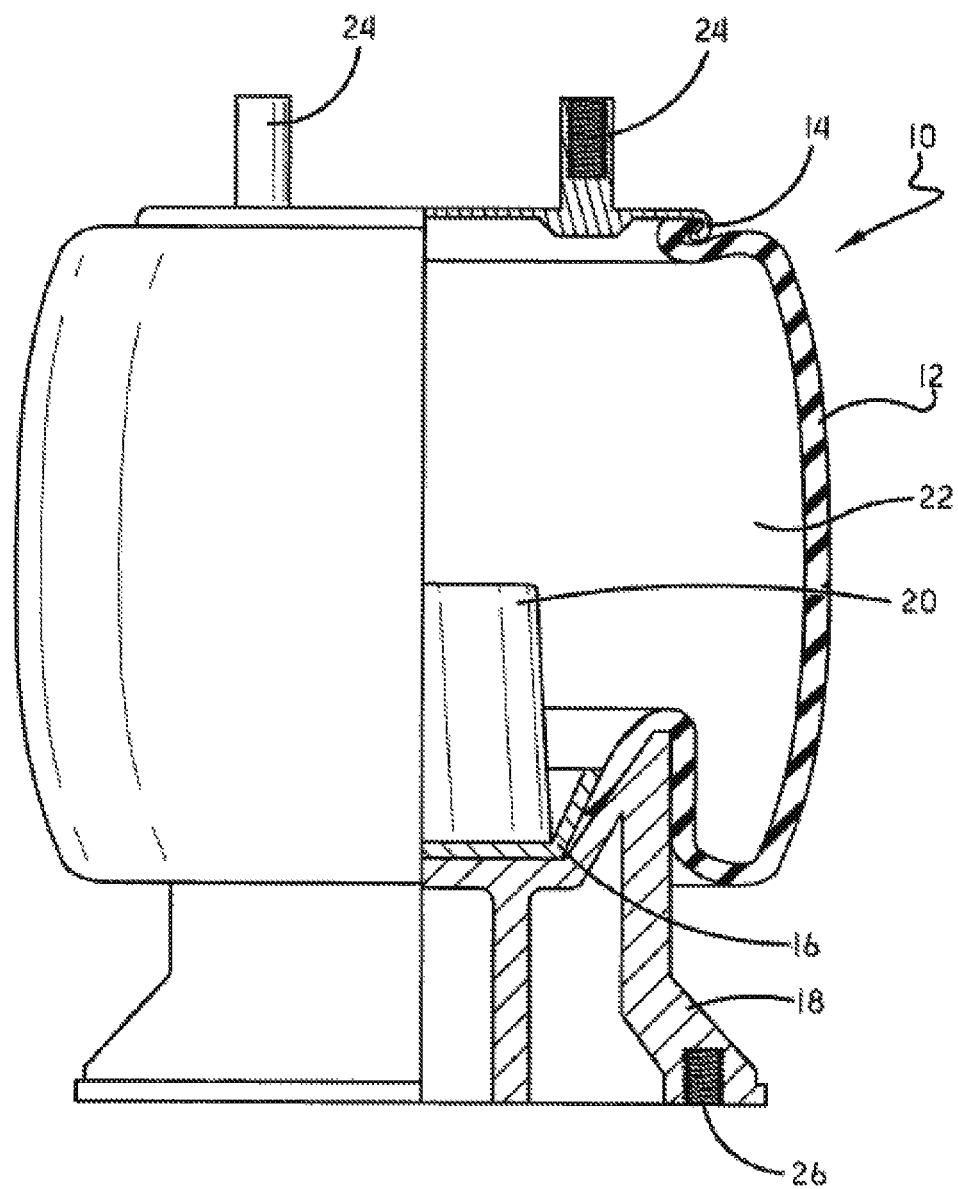
FIG. 1 is a perspective view of an exemplary air spring according to one or more embodiments of the present invention.

Embodiments of the invention are based, at least in part, on the discovery of an antioxidant precursor that can be bound to an unsaturated polymer to form a modified polymer having an antioxidant precursor functional group. The modified polymer can be incorporated into a rubber composition, and upon hydrolysis of the antioxidant precursor functional group, an antioxidant compound is released. Once released from the polymer to which it was bound, this antioxidant compound can advantageously migrate throughout the rubber composition. Embodiments of the invention therefore provide cured rubber compositions demonstrating improved properties, especially those properties impacted by oxygen and/or ozone deterioration. For example, embodiments of the invention are directed toward air spring bellows that demonstrate improved resistance to crack growth.

Antioxidant Precursor

The antioxidant precursors of one or more embodiments of the invention include those compounds that contain a substituent that can be reacted with an unsaturated polymer and a substituent that can be cleaved to yield a hindered phenol. In one or more embodiments, the antioxidant precursors include those compounds defined by the formula

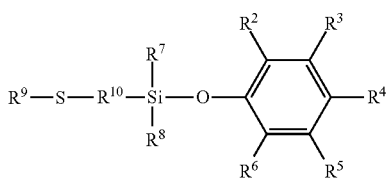

where $R^2$ through $R^6$ are each independently a hydrogen atom or a monovalent organic group, $R^7$ and $R^8$ are each independently a monovalent organic group, $R^9$ is a hydrogen atom or a blocking group, and $R^{10}$ is a covalent bond or a divalent organic group, with the proviso that at least one of $R^2$ and $R^6$ are sterically bulky groups. In certain embodiments, $R^2$ has from 1 to about 4 carbon atoms. In certain embodiments, $R^4$ has from 1 to about 4 carbon atoms. In particular embodiments, at least one of R7 and R8 is a hydrocarbyloxy group.

In one or more embodiments, the monovalent organic groups of the antioxidant precursors include hydrocarbyl groups such as, but not limited to alkyl, cycloalkyl, substituted cycloalkyl, alkenyl, cycloalkenyl, substituted cycloalkenyl, aryl, allyl, substituted aryl, aralkyl, alkaryl, and alkynyl groups. In particular embodiments, each group may contain from 1 carbon atom, or the appropriate minimum number of carbon atoms to form the group, up to 20 carbon atoms. Substituted hydrocarbyl groups include a hydrocarbyl groups in which one or more hydrogen atoms have been replaced by a substituent such as an alkyl group. In one or more embodiments, hydrocarbyl groups may contain heteroatoms such as, but not limited to, nitrogen, oxygen, silicon, sulfur, and phosphorus atoms.

In one or more embodiments, the monovalent organic groups of the antioxidant precursors include hydrocarbyloxy groups such as, but not limited to alkyloxy, cycloalkyloxy, substituted cycloalkyloxy, alkenyloxy, cycloalkenyloxy, substituted cycloalkenyloxy, aryloxy, allyloxy, substituted aryloxy, aralkyloxy, alkaryloxy, and alkynyloxy groups. In particular embodiments, each group may contain from 1 carbon atom, or the appropriate minimum number of carbon atoms to form the group, up to 20 carbon atoms. Substituted hydrocarbyloxy groups include a hydrocarbyloxy groups in which one or more hydrogen atoms have been replaced by a substituent such as an alkyl group. In one or more embodiments, the hydrocarbyloxy groups may contain heteroatoms such as, but not limited to, nitrogen, oxygen, silicon, sulfur, and phosphorus atoms.

The skilled person understands that sterically bulky groups include those monovalent groups that offer stearic hindrance to the compound to which they are attached. Non-limiting examples of sterically bulky organic groups include isopropyl, isobutyl, t-butyl, neopentyl, 2-ethylhexyl, cyclohexyl, 1-methylcyclopentyl, and 2,6-dimethylphenyl groups.

In one or more embodiments, divalent organic groups include hydrocarbylene groups or substituted hydrocarbylene groups such as, but not limited to, alkylene, cycloalkylene, substituted alkylene, substituted cycloalkylene, alkenylene, cycloalkenylene, substituted alkenylene, substituted cycloalkenylene, arylene, and substituted arylene groups. In one or more embodiments, each group may contain from 1 carbon atom, or the appropriate minimum number of carbon atoms to form the group, up to about 20 carbon atoms. Substituted hydrocarbylene groups include a hydrocarbylene groups in which one or more hydrogen atoms have been replaced by a substituent such as an alkyl group. The divalent organic groups may also contain one or more heteroatoms such as, but not limited to, nitrogen, oxygen, boron, silicon, sulfur, and phosphorus atoms.

In one or more embodiments, blocking groups include those groups that can bond to a sulfur atom and thereby block the reactivity of the sulfur atom, especially toward unsaturated molecules, and yet can be later released (i.e. unblock the sulfur atom) to thereby allow the sulfur atom to react, especially with an unsaturated molecule. In one or more embodiments, the blocking group includes an unsaturated heteroatom or carbon atom chemically bound directly to sulfur via a single bond. These blocking groups optionally may be substituted with one or more carboxylate ester or carboxylic acid functional groups. Blocking groups of this nature are well known in the art as described in U.S. Pat. Nos. 6,127,468; 6,204,339; 6,528,673; 6,635,700; 6,649,684; 6,683,135, which are incorporated herein by reference.

In one or more embodiments, types of antioxidant precursor compounds include dihydrocarbyloxy-2,4-di-tert-buylphenoxy-[3-mercapto hydrocarbylsilanes], hydrocarbyloxy-2,4-di-tert-butylphenoxy-[3-mercapto hydrocarbyl]-hydrocarbylsilanes, dihydrocarbyloxy-2,4-di-tert-buylphenoxy-[3-hydrocarbanolymercapto hydrocarbylsilanes], and hydrocarbyloxy-2,4-di-tert-butyl-phenoxy-[3-hydrocarbanolymercapto hydrocarbyl]-hydrocarbylsilanes.

Exemplary dihydrocarbyloxy-2,4-di-tert-buylphenoxy-[3-mercapto hydrocarbylsilanes] include diethoxy-2,4-di-tert-butylphenoxy-[3-mercapto propylsilane], dimethoxy-2,4-di-tert-butylphenoxy-[3-mercapto propylsilane], dipropoxy-2,4-di-tert-butyl phenoxy-[3-mercapto propylsilane], dibutoxy-2,4-di-tert-butylphenoxy-[3-mercapto propylsilane], diethoxy-2,4-di-tert-butylphenoxy-[3-mercapto heyxlsilane], dimethoxy-2,4-di-tert-butylphenoxy-[3-mercapto hexylsilane], dipropoxy-2,4-di-tert-butyl phenoxy-[3-mercapto hexylsilane], dibutoxy-2,4-di-tert-butylphenoxy-[3-mercapto hexylsilane], diethoxy-2,4-di-tert-butylphenoxy-[3-mercapto phenylsilane], dimethoxy-2,4-di-tert-butylphenoxy-[3-mercapto phenylsilane], dipropoxy-2,4-di-tert-butylphenoxy-[3-mercapto phenylsilane], dibutoxy-2,4-di-tert-butylphenoxy-[3-mercapto phenylsilane], diethoxy-2,4-di-isopropylphenoxy-[3-mercapto propylsilane], dimethoxy-2,4-di-isopropylphenoxy-[3-mercapto propylsilane], dipropoxy-2,4-di-isopropylphenoxy-[3-mercapto propylsilane], and dibutoxy-2,4-di-isopropylphenoxy-[3-mercapto propylsilane].

Exemplary hydrocarbyloxy-2,4-di-tert-butylphenoxy-[3-mercapto hydrocarbyl]-hydrocarbylsilanes include ethoxy-2,4-di-tert-butylphenoxy-[3-mercapto propyl] ethylsilane, methoxy-2,4-di-tert-butylphenoxy-[3-mercapto propyl] methylsilane, propoxy-2,4-di-tert-butyl phenoxy-[3-mercapto propyl] propylsilane, butoxy-2,4-di-tert-butylphenoxy-[3-mercapto propyl] butylsilane, ethoxy-2,4-di-tert-butylphenoxy-[3-mercapto heyxl] ethylsilane, methoxy-2,4-di-tert-butylphenoxy-[3-mercapto hexyl] methylsilane, propoxy-2,4-di-tert-butyl phenoxy-[3-mercapto hexyl]propylsilane, butoxy-2,4-di-tert-butylphenoxy-[3-mercapto hexyl] butylsilane, ethoxy-2,4-di-tert-butylphenoxy-[3-mercapto phenyl] ethylsilane, methoxy-2,4-di-tert-butylphenoxy-[3-mercapto phenyl] methylsilane, propoxy-2,4-di-tert-butylphenoxy-[3-mercapto phenyl] propylsilane, butoxy-2,4-di-tert-butylphenoxy-[3-mercapto phenyl]butylsilane, ethoxy-2,4-di-isopropylphenoxy-[3-mercapto propyl] ethylsilane, methoxy-2,4-di-isopropylphenoxy-[3-mercapto propyl] methylsilane, propoxy-2,4-di-isopropylphenoxy-[3-mercapto propyl] propylsilane, and butoxy-2,4-di-isopropylphenoxy-[3-mercapto propyl] butylsilane.

Exemplary dihydrocarbyloxy-2,4-di-tert-buylphenoxy-[3-hydrocarbanolymercapto hydrocarbylsilanes] include diethoxy-2,4-di-tert-butylphenoxy-[3-octanoylmercapto propylsilane], dimethoxy-2,4-di-tert-butylphenoxy-[3-octanoylmercapto propylsilane], dipropoxy-2,4-di-tert-butyl phenoxy-[3-octanoylmercapto propylsilane], dibutoxy-2,4-di-tert-butylphenoxy-[3-octanoylmercapto propylsilane], diethoxy-2,4-di-tert-butylphenoxy-[3-octanoylmercapto heyxlsilane], dimethoxy-2,4-di-tert-butylphenoxy-[3-octanoylmercapto hexylsilane], dipropoxy-2,4-di-tert-butyl phenoxy-[3-octanoylmercapto hexylsilane], dibutoxy-2,4-di-tert-butylphenoxy-[3-octanoylmercapto hexylsilane], diethoxy-2,4-di-tert-butylphenoxy-[3-octanoylmercapto phenylsilane], dimethoxy-2,4-di-tert-butylphenoxy-[3-octanoylmercapto phenylsilane], dipropoxy-2,4-di-tert-butylphenoxy-[3-octanoylmercapto phenylsilane], dibutoxy-2,4-di-tert-butylphenoxy-[3-octanoylmercapto phenylsilane], diethoxy-2,4-di-isopropylphenoxy-[3-octanoylmercapto propylsilane], dimethoxy-2,4-di-isopropylphenoxy-[3-octanoylmercapto propylsilane], dipropoxy-2,4-di-isopropylphenoxy-[3-octanoylmercapto propylsilane], and dibutoxy-2,4-di-isopropylphenoxy-[3-octanoylmercapto propylsilane].

Exemplary hydrocarbyloxy-2,4-di-tert-butylphenoxy-[3-hydrocarbanolymercapto hydrocarbyl]-hydrocarbylsilanes include ethoxy-2,4-di-tert-butylphenoxy-[3-octanoylmercapto propyl] ethylsilane, methoxy-2,4-di-tert-butylphenoxy-[3-octanoylmercapto propyl] methylsilane, propoxy-2,4-di-tert-butyl phenoxy-[3-octanoylmercapto propyl] propylsilane, butoxy-2,4-di-tert-butylphenoxy-[3-octanoylmercapto propyl] butylsilane, ethoxy-2,4-di-tert-butylphenoxy-[3-octanoylmercapto heyxl] ethylsilane, methoxy-2,4-di-tert-butylphenoxy-[3-octanoylmercapto hexyl] methylsilane, propoxy-2,4-di-tert-butyl phenoxy-[3-octanoylmercapto hexyl] propylsilane, butoxy-2,4-di-tert-butylphenoxy-[3-octanoylmercapto hexyl] butylsilane, ethoxy-2,4-di-tert-butylphenoxy-[3-octanoylmercapto phenyl] ethylsilane, methoxy-2,4-di-tert-butylphenoxy-[3-octanoylmercapto phenyl] methylsilane, propoxy-2,4-di-tert-butylphenoxy-[3-octanoylmercapto phenyl] propylsilane, butoxy-2,4-di-tert-butylphenoxy-[3-octanoylmercapto phenyl] butylsilane, ethoxy-2,4-di-isopropylphenoxy-[3-octanoylmercapto propyl] ethylsilane, methoxy-2,4-di-isopropylphenoxy-[3-octanoylmercapto propyl] methylsilane, propoxy-2,4-di-isopropylphenoxy-[3-octanoylmercapto propyl] propylsilane, and butoxy-2,4-di-isopropylphenoxy-[3-octanoylmercapto propyl] butylsilane.

Preparation of Antioxidant Precursor

In one or more embodiments, the antioxidant precursor may be prepared by reacting a mercaptosiloxane with a phenol compound (e.g. hindered phenol compound). This reaction may take place in the presence of a condensation catalyst such as, but not limited to, polymeric ion exchange resins, such as those that include cationic functionality (e.g. Dowex available from Dow Chemical Company). In one or more embodiments, the reaction between the mercaptosiloxane and the phenol compound takes place at a temperature and pressure sufficient to distill water formed during the reaction.

Modified Polymer with Antioxidant Precursor Functional Group

As indicated above, the antioxidant precursor compound can be bound to a polymer or polymer network to form a modified polymer or polymer network having an antioxidant precursor functional group. In or more embodiments, the antioxidant functional group is covalently bound (i.e. tethered) to the polymer or network through the sulfur atom of the precursor compound.

In one or more embodiments, the modified polymer or polymer network containing an antioxidant precursor functional group may be defined by the formula

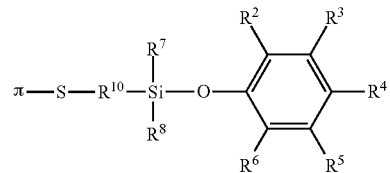

where $R^2$ through $R^6$ are each independently a hydrogen atom or a monovalent organic group, $R^7$ and $R^8$ are each independently a monovalent organic group, $R^{10}$ is a covalent bond or a divalent organic group, with the proviso that at least one of $R^2$ and $R^6$ are sterically bulky groups, and π is a polymer chain or a cross-linked polymer network.

In one or more embodiments, the concentration of the antioxidant precursor functional group on the modified polymer of the invention can be defined in terms of the weight of the hindered phenoxy functionality to the weight of the overall polymer. In one or more embodiments, the concentration may be from about 0.02 to about 20, in other embodiments from about 0.5 to about 12, and in other embodiments from about 1 to about 5 weight parts hindered phenoxy functionality to weight of the polymer.

The skilled person recognizes that the antioxidant precursor may not chemically react with the unsaturated polymer until the entire composition undergoes curing, and therefore the antioxidant precursor will ultimately be bound to a cured polymer network in lieu of an individual polymer molecule. Accordingly, reference will be made to both a polymer and polymer network with the understanding that the polymer network derives from the curing or cross-linking of the unsaturated polymer.

In one or more embodiments, the polymer chain (π) of the modified polymer contains unsaturation. In these or other embodiments, the polymer chain is vulcanizable. The polymer chain can have a glass transition temperature ($T_g$) that is less than 0° C., in other embodiments less than −20° C., and in other embodiments less than −30° C. In one embodiment, the polymer chain may exhibit a single glass transition temperature.

In one or more embodiments, the polymer chain (π) may be medium or low cis polydienes (or polydiene copolymers) including those prepared by anionic polymerization techniques. These polydienes can have a cis-1,4-linkage content of from about 10% to 60%, in other embodiments from about 15% to 55%, and in other embodiments from about 20% to about 50%, where the percentages are based upon the number of diene mer units in the cis configuration versus the total number of diene mer units. These polydienes may also have a 1,2-linkage content (i.e. vinyl content) from about 10% to about 90%, in other embodiments from about 10% to about 60%, in other embodiments from about 15% to about 50%, and in other embodiments from about 20% to about 45%, where the percentages are based upon the number of diene mer units in the vinyl configuration versus the total number of diene mer units. The balance of the diene units may be in the trans-1,4-linkage configuration.

In particular embodiments, the polymer chain ($\pi$) may be a copolymer of butadiene, styrene, and optionally isoprene. These may include random copolymers. In other embodiments, the polymers are block copolymers of polybutadiene, polystyrene, and optionally polyisoprene. In particular embodiments, these polymers are hydrogenated or partially hydrogenated. In one or more embodiments, the polymer chain ($\pi$) is a copolymer of styrene and conjugated diene where the molar ratio of styrene mer units to conjugated diene mer units is from about 1:1 to about 0.05:1, in other embodiments from about 0.7:1 to about 0.1:1, and in other embodiments from about 0.5:1 to about 0.2:1.

In one or more embodiments, the polymer chain is a copolymer of a isobutylene and a diene such as isoprene. The may include random copolymers. In particular embodiments, these polymers are hydrogenated or partially hydrogenated. In one or more embodiments, the polymer chain ($\pi$) is a copolymer of isobutylene and conjugated diene where the molar ratio of isobutylene mer units to conjugated diene mer units is from about 60:1 to about 10:1, in other embodiments from about 50:1 to about 15:1, and in other embodiments from about 40:1 to about 20:1.

In one or more embodiments, the polymer chain $\pi$ may include natural rubber. In one or more embodiments, the polymer chain $\pi$ is a synthetic polymer selected from the group consisting of polybutadiene, polyisoprene, poly(styrene-co-butadiene), poly(styrene-co-butadiene-co-isoprene), poly(isoprene-co-styrene), and poly(butadiene-co-isoprene), polyisoprene, poly(isobutylene-co-isoprene), polychloroprene (i.e. neoprene), poly(ethylene-co-propylene), poly(styrene-co-isoprene-co-butadiene), poly(ethylene-co-propylene-co-diene), polysulfide rubber, acrylic rubber, urethane rubber, nitrile rubber (i.e. poly(acrylonitrile-co-butadiene)), hydrogenated nitrile rubber, silicone rubber, epichlorohydrin rubber, and chlorinated polyethylene.

In one or more embodiments, the number average molecular weight ($M_n$) of the polymer chains may be from about 1 to about 1,000 in other embodiments from about 5 to about 1,000, in other embodiments from about 50 to about 500, and in other embodiments from about 100 to about 300 kg/mol, as determined by using gel permeation chromatography (GPC) calibrated with polystyrene standards and Mark-Houwink constants for the polymer in question. The polydispersity ($M_w/M_n$) of these polymers may be from about 1.0 to about 3.0, and in other embodiments from about 1.1 to about 2.0.

Preparation of Modified Polymer

In one or more embodiments, the modified polymer may be prepared by solid-state mixing the antioxidant precursors defined herein with an unsaturated polymer to form a mixture, and then subjecting the mixture to conditions that allow the sulfur atom of the antioxidant precursor to react with a double bond within the unsaturated polymer.

In one or more embodiments, the unsaturated polymers include those discussed above with respect to the modified polymer. For example, the unsaturated polymers may include natural rubber and synthetic polymers such as, but not limited to, polybutadiene, polyisoprene, poly(styrene-co-butadiene), poly(styrene-co-butadiene-co-isoprene), poly(isoprene-co-styrene), and poly(butadiene-co-isoprene), polyisoprene, poly(isobutylene-co-isoprene), polychloroprene (i.e. neoprene), poly(ethylene-co-propylene), poly(styrene-co-isoprene-co-butadiene), poly(ethylene-co-propylene-co-diene), polysulfide rubber, acrylic rubber, urethane rubber, nitrile rubber (i.e. poly(acrylonitrile-co-butadiene)), epichlorohydrin rubber, and chlorinated polyethylene.

In one or more embodiments, the step of combining the antioxidant precursor compound and the unsaturated polymer takes place at temperatures below 150, in other embodiments below 110, and in other embodiments below 50° C.

Vulcanizable Composition

In one or more embodiments, where the mixture containing the antioxidant precursor and the unsaturated rubber further includes a curative for the rubber, the mixture may be referred to as a vulcanizable composition. As the skilled person will appreciate, the antioxidant precursor compound may be present within the vulcanizable composition or, where it has reacted and attached itself to a polymer, a polymer-bound antioxidant precursor may be present within the vulcanizable composition. In one or more embodiments, the polymer-bound antioxidant precursor may be defined by the formula

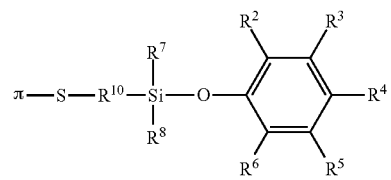

where $R^2$ through $R^6$ are each independently a hydrogen atom or a monovalent organic group, $R^7$ and $R^8$ are each independently a monovalent organic group, $R^{10}$ is a covalent bond or a divalent organic group, with the proviso that at least one of $R^2$ and $R^6$ are sterically bulky groups, $R^9$ is a hydrogen atom or a blocking group, and $\pi$ is a polymer chain.

In one or more embodiments, the vulcanizable composition may further include additional unsaturated rubber, saturated rubber (i.e. hydrogenated rubber), fillers, plasticizers, antioxidants, oils, curatives, processing aids, and other additives that are conventionally employed in rubber compositions. Further, especially in those embodiments where the antioxidant precursor compound includes a blocking group bonded to the sulfur atom, a deblocking agent may be included within the vulcanizable composition.

In one or more embodiments, the additional rubber included within the vulcanizable composition may include those reference above. For example, these additional rubbers may include natural rubber and synthetic polymers such as, but not limited to, polybutadiene, polyisoprene, poly(styrene-co-butadiene), poly(styrene-co-butadiene-co-isoprene), poly(isoprene-co-styrene), and poly(butadiene-co-isoprene), polyisoprene, poly(isobutylene-co-isoprene), polychloroprene (i.e. neoprene), poly(ethylene-co-propylene), poly(styrene-co-isoprene-co-butadiene), poly(ethylene-co-propylene-co-diene), polysulfide rubber, acrylic rubber, urethane rubber, nitrile rubber (i.e. poly(acrylonitrile-co-butadiene)), hydrogenated nitrile rubber, silicone rubber, epichlorohydrin rubber, and chlorinated polyethylene.

In particular embodiments, especially where the vulcanizable composition is employed in the manufacture of one or more layers of an air spring bellow, the additional rubber may include one or more of polychloroprene, poly(styreneco-butadiene) and poly(isobutylene-co-isoprene). Elastomers that are useful in vulcanizable compositions for air spring bellows are further described in co-pending U.S. Application Publication No. 2010/0117274 and International Application Publication No. WO 2011/0884488, both of which are incorporated herein by reference in their entirety.

In one or more embodiments, the vulcanizable composition may include one or more fillers. Fillers may include organic and inorganic fillers. For example, the vulcanizable composition may include carbon black. In particular embodiments, the carbon black may include virtually pure elemental carbon in the form of colloidal particles that are produced by incomplete combustion or thermal decomposition of gaseous or liquid hydrocarbons under controlled conditions. In particular embodiments, a reinforcing carbon black is used; in other embodiments, non-reinforcing carbon black is used; and in other embodiments, a blend of reinforcing and non-reinforcing carbons are employed. Examples of reinforcing carbon blacks include N300 or N330 carbon black. In other embodiments, non-reinforcing carbon blacks include those conforming to the characteristics of ASTM N550 and ASTM N762.

In one or more embodiments, the filler may include silica. Useful forms of silica (silicon dioxide) include crystalline and amorphous silica. The crystalline form of silica includes quartz, tridymite and cristobalite. Amorphous silica may occur when the silicon and oxygen atoms are arranged in an irregular form as identified by X-ray diffraction. In one or more embodiments, the silica is a precipitated silica. In these or other embodiments, fumed silica is employed. Commercially available forms of silica are available from PPG Industries, Inc. (Monroeville, Pa.), Degussa Corporation (Parsippany, N.J.) and J.M. Huber Corporation (Atlanta, Ga.). One useful commercial product is Rubbersil® RS-150, which is characterized by a BET surface area of 150 m$^2$/g, tapped density of 230 g/liter, pH (5% in water suspension) of 7, SiO$_2$ content of 98%, Na$_2$SO$_4$ content of 2%, and Al$_2$O$_3$ content of 0.2%.

Other organic fillers include coal filler and ground recycled rubber. Other useful inorganic fillers include clays, talc, mica, titanium dioxide, and calcium carbonate. Useful clays include hydrated aluminum silicates.

In one or more embodiments, especially where the filler incudes silica, a coupling and/or shielding agent may be included. Useful silica coupling agents include bifunctional silica coupling agents having a moiety (e.g., an alkoxysilyl group) reactive with the silica surface, and a moiety (e.g., a mercapto, amino, vinyl, epoxy or sulfide group) that binds to the elastomer. Well known examples of such silica coupling agents are mercaptosilanes, bis(trialkoxysilylorgano)polysulfides, such as bis(3-triethoxysilylpropyl)tetrasulfide, which is sold commercially as Si69 (Degussa), and 3-thiocyanatopropyl trimethoxysilane. Useful shielding agents include compounds that improve the dispersion of the filler in the vulcanizable composition, and may therefore be referred to as a dispersing aid. Examples of shielding agents include alkyl alkoxysilanes, fatty acid esters of a hydrogenated or non-hydrogenated C$_5$ or C$_6$ sugar, polyoxyethylene derivatives of a fatty acid ester of a hydrogenated or non-hydrogenated C$_5$ or C$_6$ sugar, and mixtures thereof, as well as mineral or non-mineral additional fillers.

In one or more embodiments, the vulcanizable composition of this invention may include an additional antioxidant and/or antidegradant. Useful antioxidants include bisphenol type antioxidants, diphenylamines, and zinc salts. Examples of antidegradants include 4- and 5-methyl-2-mercaptobenzimidazole (MMBI), mixed diaryl-p-phenylene type antidegradants, IPPD, or N-isopropyl-N'-phenyl-p-phenylenediamine, and 6PPD, or N-(1,3-dimethylbutyl)-N-phenyl-p-phenylenediamine.

In one or more embodiments, the vulcanizable compositions may also include low oil swell factices, or vulcanized oils. In specific embodiments, these compounds include sulfur vulcanized vegetable oils. In one or more embodiments, plasticizers, which may also be referred to as softeners, include, but are not limited to, fatty acids, vegetable oils, petroleum products, coal tar products, pine products, esters, and resins. In particular embodiments, the plasticizers include esters such as dicapryilphthalate, butylcuminate, dibutylphthalate, butyllactate, glycerol chlorobenzoate, methylricinoleate, octyloleate, dioctylphthalate, or dioctylsebacate.

In one or more embodiments, the vulcanizable compositions of this invention may include a tackifier or tackifier resin. Natural or synthetic resins may be employed. In particular embodiments, a nitrile rubber latex is employed as a tackifier.

In one or more embodiments, the vulcanizable composition of this invention includes a curative, or cure package. The cure package includes a sulfur-based compound and may also include other optional ingredients. Although one having skill in the art may appreciate other possible cure packages, an exemplary cure package includes sulfur, TMTD, zinc oxide, Vulkanox MB2 (AO2), and IPPD. In one or more embodiments, the vulcanizable composition of this invention may include stearic acid. In one or more embodiments, the vulcanizable composition of this invention may include magnesium oxide (MgO).

In one or more embodiments, deblocking agents, which are sometimes referred to as deprotection agents, may include N,N'-diphenylguanidine, ethanolamines, ethyleneamines, ethylene glycol, polyethylene glycols, propylene glycol, polypropylene glycols, mixed ethylene-propylene glycols, alkyl-terminated glycols, glycerol, trimethylol alkanes, pentaerythritol, anilines, phenylene diamines, phenol, catechol, dihydroquinone, resorcinol, aminophenols, 1,3-diaminopropane, 1,4-diaminobutane, 1,5-diaminopentane, 1,6-diaminohexane, N-(3-aminopropyl)-1,3-propanediamine (3,3'-iminobispropylamine), 3-amino-1-propanol, imidazole, benzimidazole, aminobenzimidazole, pyrrole, indole, pyrazole, triazole, benzotriazole, and mixtures thereof. In one embodiment, the deblocking agents include N,N'-diphenylguanidine (DPG), glycerol, N-(3-aminopropyl)-1,3-propanediamine (3,3'-iminobispropylamine), diethylene triamine, triethylene tetramine, trimethylol propane, and ethylene glycol. In another embodiment, the deblocking agents include DPG, glycerol, diethylene glycol, and trimethylol propane. Deblocking agents are generally known as described in U.S. Pat. Nos. 6,579,949 and 6,683,135, which are incorporated herein by reference.

Ingredient Amounts

In one or more embodiments, the vulcanizable compositions of this invention include a sufficient amount of vulcanizable rubber so as to achieve a technologically useful rubber articles such as one or more layers of an air spring bellow. In one or more embodiments, the overall vulcanizable composition includes at least 35% by weight, in other embodiments at least 40% by weight, and in other embodiments at least 45% by weight vulcanizable rubber. In these or other embodiments, the overall vulcanizable composition of matter includes less than 99%, in other embodiments less than 90%, and in other embodiments less than 75% by weight vulcanizable rubber.

In one or more embodiments, the vulcanizable compositions of the present invention include at least about 0.2, in other embodiments at least about 0.5, and in other embodiments at least about 1 parts by weight (pbw) antioxidant precursor per 100 parts by weight rubber (phr). In these or other embodiments, the vulcanizable compositions include at most 20, in other embodiments at most 15, and in other embodiments at most 10 pbw antioxidant precursor phr. In one or more embodiments, the vulcanizable composition may include from about 0.2 to about 20, in other embodiments from about 0.3 to about 15, and in other embodiments from about 0.4 to about 10 pbw antioxidant precursor phr.

In one or more embodiments, the vulcanizable compositions may include at least 0.001 wt. %, in other embodiments at least 0.005 wt. %, and in other embodiments at least 0.01 wt. % antioxidant precursor, based on the total weight of the composition. In these or other embodiments, the vulcanizable compositions may include less than 5 wt. %, in other embodiments less than 3 wt. %, and in other embodiments less than 2 wt. % antioxidant precursor, based upon the weight of the rubber. In these or other embodiments, the vulcanizable compositions may include from about 0.001 to about 5 wt. %, in other embodiments from about 0.005 to about 3 wt. %, and in other embodiments from about 0.01 to about 2 wt. % antioxidant precursor, based on the total weight of the rubber.

In one or more embodiments, the vulcanizable compositions may include at least about 20, in other embodiments at least about 30, and in other embodiments at least about 40 parts by weight (pbw) filler per 100 parts by weight rubber (phr). In these or other embodiments, the vulcanizable compositions include at most 130, in other embodiments at most 100, and in other embodiments at most 70 pbw filler phr. In one or more embodiments, the vulcanizable composition may include from about 20 to about 130, in other embodiments from about 30 to about 100, and in other embodiments from about 40 to about 70 pbw filler phr.

Method of Preparing Vulcanizable Composition

In one or more embodiments, the vulcanizable compositions of the invention can be prepared by using known mixing techniques for the preparation of rubber compositions. For example, the compositions can be prepared by using conventional rubber compounding equipment such as Brabender, Banbury, Werner-Pfleiderer, Sigma-blade mixers, two-roll mills, or other mixers suitable for forming viscous, relatively uniform admixtures. Mixing techniques depend on a variety of factors such as the specific types of polymers used, and the fillers, processing oils, waxes, and other ingredients used. In one or more embodiments, the ingredients can be added together in a single stage. In other embodiments, an incremental procedure can be used whereby the rubber and part of the ingredients are added first, and the remaining ingredients are added in additional increments. In one or more embodiments, two-stage mixing can be employed. Mixing cycles generally range from about 2 to 10 minutes.

In one or more embodiments, the antioxidant precursor is added after high-shear and/or high-temperature mixing. As the skilled person recognizes, rubber compositions, especially those including filler materials, are initially mixed at high temperatures and at high shear in order to incorporate filler into the composition. Once the filler has been adequately dispersed, reactive compounds, such as coupling agents and curatives, are added and blending into the composition using lower temperatures and low shear in an effort to prevent premature curing (i.e. scorch) of the composition. Accordingly, in one or more embodiments, the antioxidant precursor compound is added in proximate to the addition of the curative. In one or more embodiments, the antioxidant precursor is added before the cure package is added. In other embodiments, the antioxidant precursor can be added contemporaneously with the curative. In other embodiments, the antioxidant precursor is added after the curative.

Where a deblocking agent is employed, the deblocking agent can be added at any time during the compounding process. In one or more embodiments, the deblocking agent is added during after high shear mixing as further described in U.S. Pat. No. 7,256,231, which is incorporated by reference herein.

Industrial Applicability—Air Spring Bellows

As indicated above, the vulcanizable compositions of this invention have been found to be particularly useful in the manufacture of air spring bellows. For example, FIG. 1, shows an air spring assembly designated generally by the numeral 10. The air spring assembly 10 includes flexible bellow 12, which may also be referred as airsleeve 12. Bead plate 14 is crimped to airsleeve 12 to form an airtight seal between bead plate 14 and airsleeve 12. Similarly, end closure 16 is molded to flexible airsleeve 12 to form an airtight seal between end closure 16 and airsleeve 12. End closure 16 of airsleeve 12 is affixed to piston 18 by mechanical means well known in the art, including, for example, a piston bolt (not shown). Piston 18 provides a surface for flexible airsleeve 12 to roll on during compressive (jounce) travel. Flexible air spring assembly 10 may optionally include bumper 20 to support the vehicle when there is no air in the air springs or during extreme road disturbances. Enclosed within airsleeve 12 is a volume of gas 22. Studs 24 and hole 26 are used to secure the flexible air spring assembly 10 to the mounting surface of an automobile (not shown).

Figure 2:
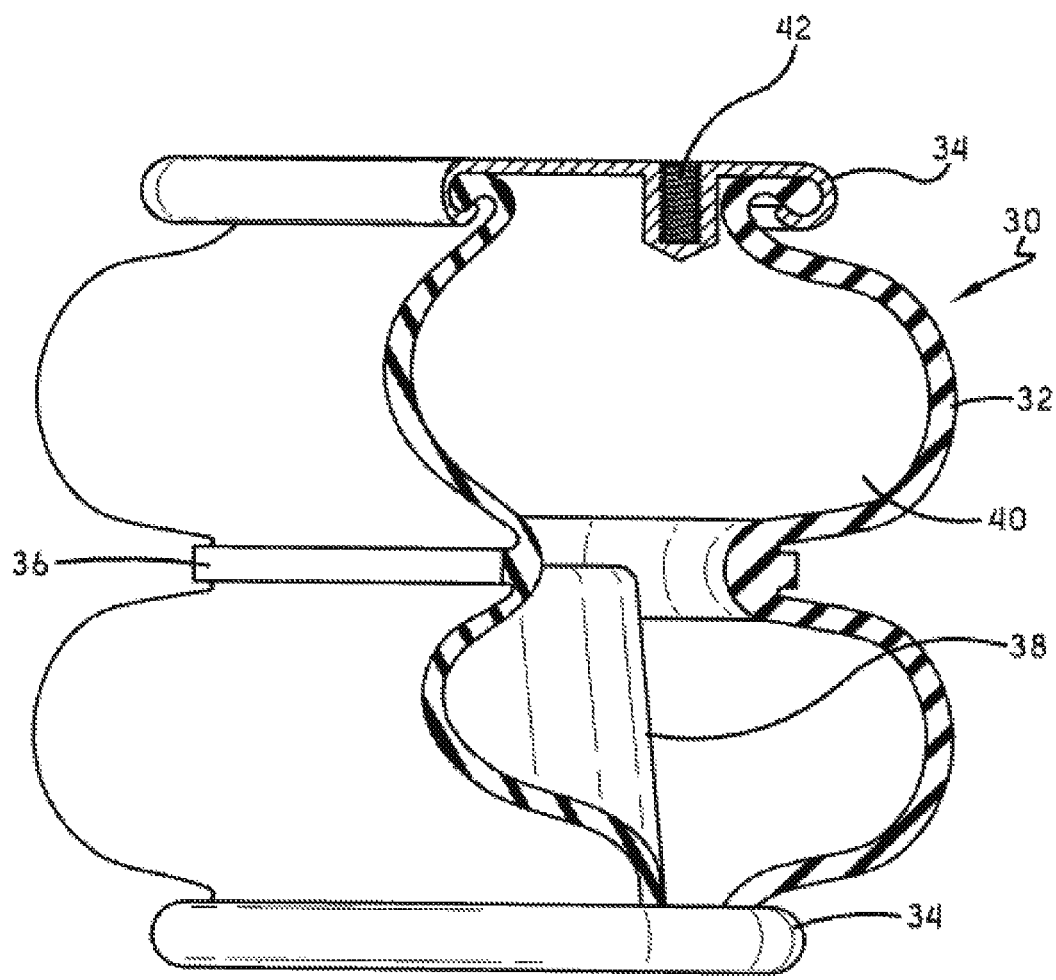
FIG. 2 is a perspective view of an exemplary air spring according to one or more embodiments of the present invention.

FIG. 2 shows an exemplary (double) convoluted air spring assembly designated generally by the numeral 30. Convoluted air spring assembly 30 includes flexible airsleeve 32. Bead plates 34 are crimped to airsleeve 32 to form an airtight seal between bead plates 34 and airsleeve 32. A girdle hoop 36 is affixed to airsleeve 32 between bead plates 34. Convoluted air spring assembly 30 may optionally include bumper 38 to support the vehicle when there is no air in the air springs or during extreme road disturbances. Enclosed within airsleeve 32 is a volume of gas 40. Blind nuts, including 42 and other blind nuts (not shown), are used to secure the convoluted air spring assembly 30 to the mounting surface of an automobile (not shown).

Figure 3:
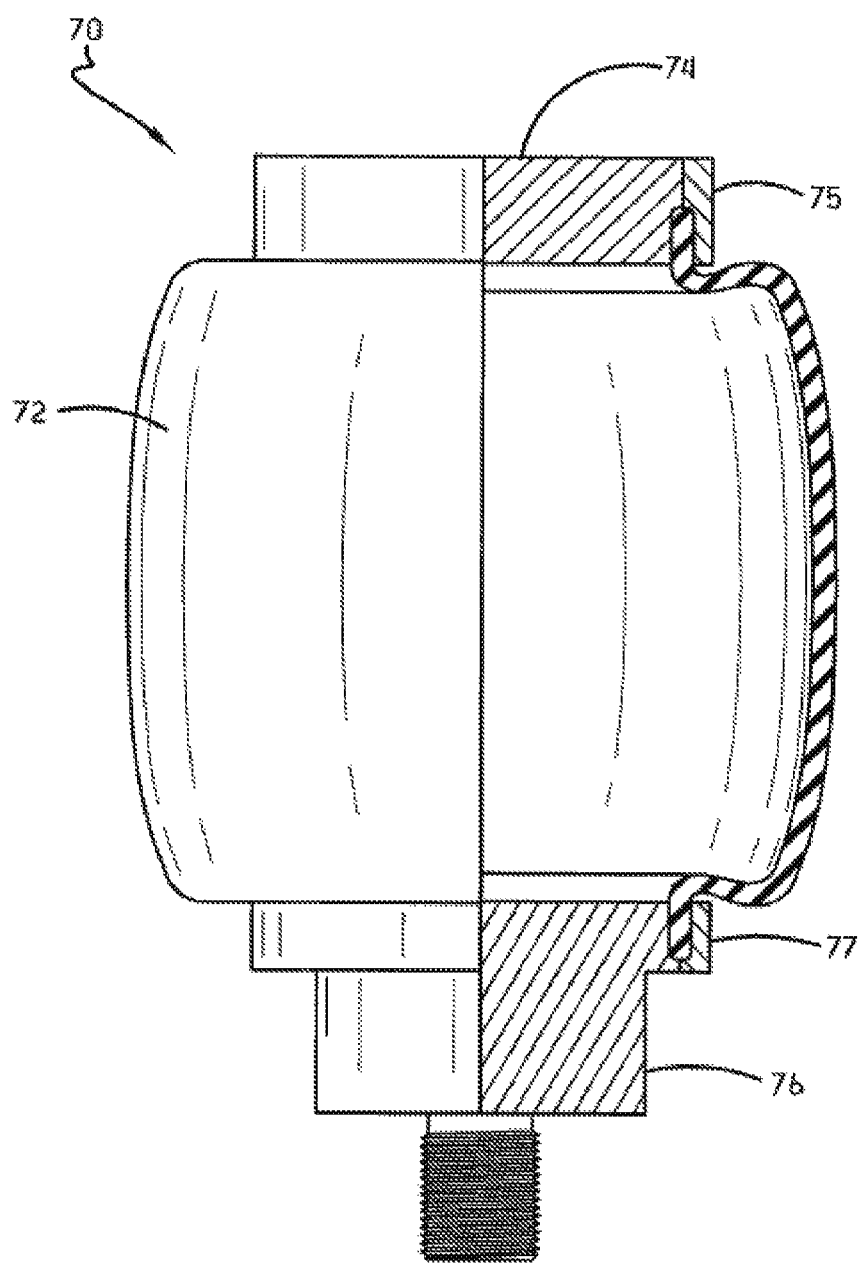
FIG. 3 is a perspective view of an exemplary air spring according to one or more embodiments of the present invention.

FIG. 3 shows an exemplary cab/seat spring assembly designated generally by the numeral 70. Cab/seat spring assembly 70 includes flexible air sleeve 72. Cab/seat plate 74 is attached to air sleeve 72 to form an air tight seal therebetween by using, for example, metal ring 75. An airtight seal can be made using known techniques such as those described in U.S. Pat. No. 6,474,630, which is incorporated herein by reference. Suspension plate 76 is likewise secured to airsleeve 72 via metal ring 77 to form an airtight seal therebetween.

Figure 4:
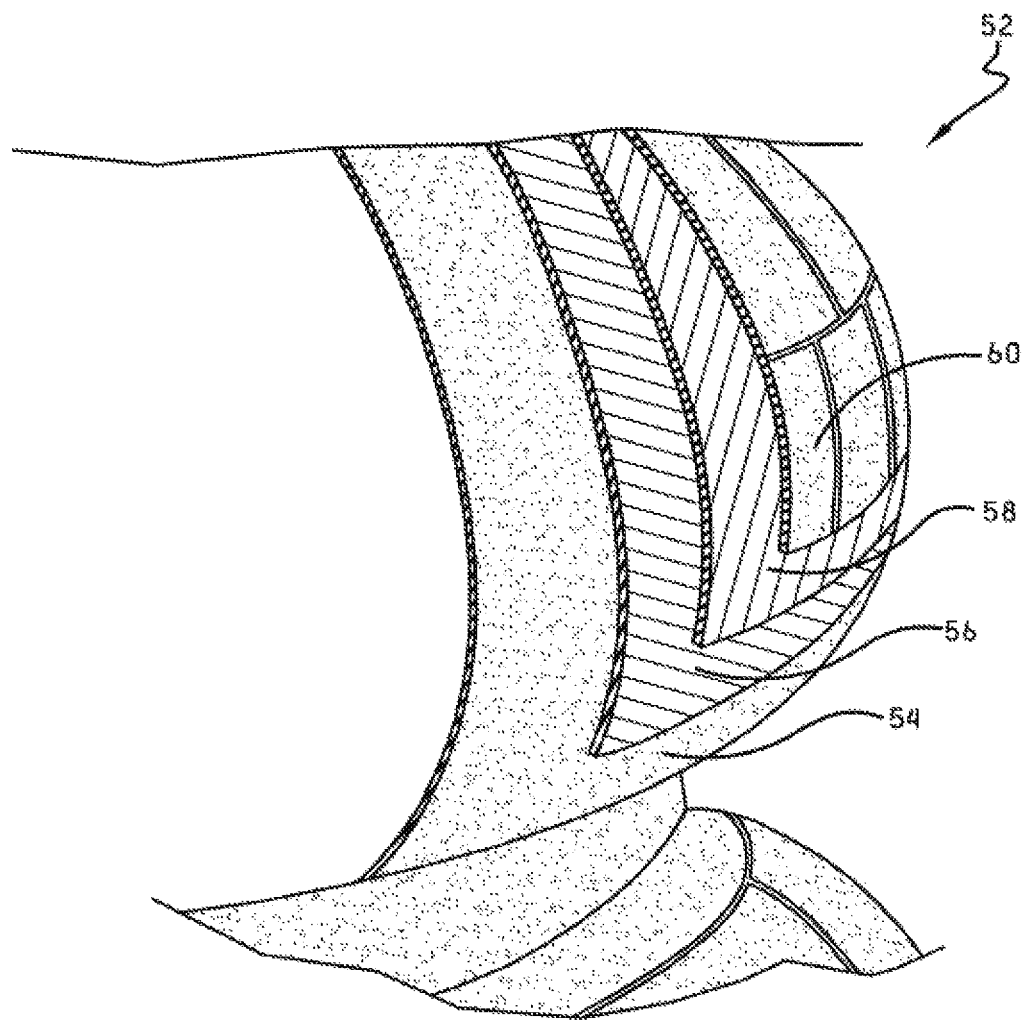
FIG. 4 is a cutaway view of an exemplary airsleeve showing its layered construction.

In one or more embodiments, airsleeves 12, 32, and 72 are made of cord-(fabric or metal) reinforced rubber and may be comprised of several layers, as shown in a cutaway view of an exemplary airsleeve 52 in FIG. 4. Exemplary airsleeve 52 features "two-ply" construction and includes four layers including: innerliner 54, first ply 56, second ply 58, and outer cover 60. Innerliner 54 and outer cover 60 may include calendared rubber. As shown, first ply 56 may include a single ply of cord-reinforced rubber with the cords at a specific bias angle, and second ply 58 may include a single ply of fabric-reinforced rubber with the same bias angle laid opposite that of first ply 56.

Thus in one or more embodiments, each layer of the bellow may contain an elastomeric, i.e, rubber component. The rubber component of each layer may be the same or different. According to the present invention, at least one layer of the bellow contains a rubber composition that includes the modified polymers of this invention, which include the antioxidant precursor functional group. In one or more embodiments, at least the cover layer of the bellow contains a rubber composition that includes a modified polymer of this invention, which include the antioxidant precursor functional group. In certain embodiments, one or more layer of the bellow laminate is prepared using the same vulcanizable formulation, which according to this invention includes an elastomer, an antioxidant precursor, and a curative.

Method of Preparing Air Bellow

In preparing an air bellow, the foregoing vulcanizable composition can be formed into a sheet by using conventional techniques such as calendaring or combined with a reinforcing cord-(fabric or metal), and the sheet can be used form one or more of the components of the bellow. Once formed, the various green rubber components can be assembled into a green air sleeve or bellow and subsequently cured by subjecting the green bellow to curing conditions. For example, the green bellow can be subjected to 120-170° C. Air spring and air sleeve constructions and methods of their manufacture are known in the art as exemplified in U.S. Pat. Nos. 7,250,203, 5,527,170, and 6,439,550, all of which are incorporated herein by reference.

Properties of Air Bellow

Advantageously, the air sleeve components fabricated from the vulcanizable compositions of this invention exhibit improved crack growth resistance, while maintaining a good balance of other properties, including tear strength. It is believed that these improved properties derive from the fact that the antioxidant precursor is bound to the rubber, which prevents premature and/or rapid migration to the surface of the air bellow. And then, over time, a hydrolysis reaction takes place cleaving the hindered phenol substituent, which allows the hindered phenol to migrate within the cured rubber composition and thereby provide useful antioxidant properties.

Use in Tires

The vulcanizable compositions of matter of this invention can be useful in preparing tire components. In particular embodiments, these tire components include carbon black filler.

A multitude of rubber curing agents (also called vulcanizing agents) may be employed, including sulfur or peroxide-based curing systems. Curing agents are described in Kirk-Othmer, ENCYCLOPEDIA OF CHEMICAL TECHNOLOGY, Vol. 20, pgs. 365-468, ($3^{rd}$ Ed. 1982), particularly Vulcanization Agents and Auxiliary Materials, pgs. 390-402, and A. Y. Coran, Vulcanization, ENCYCLOPEDIA OF POLYMER SCIENCE AND ENGINEERING, ($2^{nd}$ Ed. 1989), which are incorporated herein by reference. Vulcanizing agents may be used alone or in combination.

Other ingredients that may be employed include accelerators, oils, waxes, scorch inhibiting agents, processing aids, zinc oxide, tackifying resins, reinforcing resins, fatty acids such as stearic acid, peptizers, and one or more additional rubbers.

These rubber compositions are useful for forming tire components such as treads, subtreads, black sidewalls, body ply skins, bead filler, and the like.

In one or more embodiments, the vulcanizable rubber composition may be prepared by forming an initial masterbatch that includes the rubber component and filler (the rubber component optionally including the functionalized polymer of this invention). This initial masterbatch may be mixed at a starting temperature of from about 25° C. to about 125° C. with a discharge temperature of about 135° C. to about 180° C. To prevent premature vulcanization (also known as scorch), this initial masterbatch may exclude vulcanizing agents. Once the initial masterbatch is processed, the vulcanizing agents may be introduced and blended into the initial masterbatch at low temperatures in a final mixing stage, which preferably does not initiate the vulcanization process. For example, the vulcanizing agents may be introduced at a temperature less than 140° C., in other embodiments less than 120° C., and in other embodiments less than 110° C. Optionally, additional mixing stages, sometimes called remills, can be employed between the masterbatch mixing stage and the final mixing stage. Various ingredients including the functionalized polymer of this invention can be added during these remills. Rubber compounding techniques and the additives employed therein are generally known as disclosed in The Compounding and Vulcanization of Rubber, in Rubber Technology ($2^{nd}$ Ed. 1973).

While the present invention is described in the context of an airsleeve and an air spring used in the suspension of an automobile, one of skill in the art will appreciate that the teachings disclosed are general and the present invention may be applied to other art relating to the air spring areas. The other areas might include, for example, air springs for seats, air springs used to support truck cabs, air springs used with buses, and the like. Additional application of the present invention may be found for tire innerliners and sidewalls.

In order to demonstrate the practice of the present invention, the following examples have been prepared and tested. The examples should not, however, be viewed as limiting the scope of the invention. The claims will serve to define the invention.

EXPERIMENTAL

Example 1: Synthesis of diethoxy 2,4-di-t butyl phenoxy (3-mercaptopropyl) silane To a 500 mL round bottom flask equipped with a heating mantel, magnetic stirrer, nitrogen purge and a Dean-Stark trap was added 113.34 g of dry toluene and 2,4-di tertiary butyl phenol (43.84 g, 212 mmol) and 3-mercaptopropyl triethoxysilane (50.38 g, 211 mmol). The mixture was heated for 2 hours to distill off any water into the trap. Then to the mixture that had been cooled to 74° C. was added dry water washed Dowex® 50WX2, 50-100 mesh cationic ion exchange resin (1.80 g, 8.64 meq of acid) without any apparent ethanol evolution. Continuing heating for 20 hours and then for a total of 44 hours showed by GC-MS to have a trace of the desired 398 g/mol desired product as being formed. At this point 83.73 g of t-butyl benzene was added and heating to 184 to 190° C. as the pot temperature. Toluene and some of the t-butyl benzene was removed the temperature was increased to 220° C. over the 64 hour total reaction time. The product was decanted from the solid ion exchange resin and washed with a small amount of toluene. The wash toluene was removed with heating to 60° C. with a nitrogen purge. No sulfur odor could be detected. Analysis by GC-MS showed 70% conversion to the desired product of 2,4-dibutyl phenoxy-3-mercaptopropyl diethoxysilane with about 30% unreacted phenol.

The antioxidant of Example 1 was employed to make a rubber compositions that was cured into an air spring airsleeve (Ex. 4). Comparative samples were also prepared and tested. Comparative Ex. 2 did not contain an antioxidant. Comparative Ex. 3 differs from Ex. 4 in that a conventional antioxidant was employed, namely N-(1,3-dimethylbutyl)-N'-phenyl-p-phenylenediamine (6PPD). Comparative Ex. 5 differs from Ex. 4 in that butylphenol was employed as an antioxidant. The formulations of the compositions are shown in the table below.

TABLE 1

| Ingredient | Ex. 2 | Ex. 3 | Ex. 4 | Ex.5 |
|---|---|---|---|---|
| Natural Rubber | 50 | 50 | 50 | 50 |
| Ni-BR* | 50 | 50 | 50 | 50 |
| Carbon Black | 50 | 50 | 50 | 50 |
| ZnO | 3 | 3 | 3 | 3 |
| Stearic Acid | 2 | 2 | 2 | 2 |
| Oil | 5 | 5 | 5 | 5 |
| Master Batch Total | 160 | 160 | 160 | 160 |
| Sulfur | 2.4 | 2.4 | 2.4 | 2.4 |
| Cure accelerator | 1.25 | 1.25 | 1.25 | 1.25 |
| 6PPD | 0 | 2 | 0 | 0 |
| Ex. 1 | 0 | 0 | 2 | 0 |
| 2,4-di-t-butylphenol | 0 | 0 | 0 | 2 |
| Batch Total | 163.65 | 165.65 | 165.65 | 165.65 |

*Butadiene rubber was polymerized using nickel-based catalyst system.

Modulus and tensile strength were measured according to ASTM D 412 (1998), using an ASTM D4482 test specimen. Unaged samples were tested at 23° C. Aged samples were also tested at 23° C., after having been humidity aged for 7 days at 50° C., with 95% relative humidity.

Viscoelastic properties and cure time parameters were measured using a Monsanto MDR2000 moving die rheometer, according to ASTM D 5289. The results for the unaged samples are summarized in Table 2.

TABLE 2

| Property | Ex. 2 | Ex. 3 | Ex. 4 | Ex.5 |
|---|---|---|---|---|
| MAXIMUM STRESS | 18.7 | 18.6 | 18.2 | 18.6 |
| 50% MODULUS (MPa) | 1.68 | 1.59 | 1.59 | 1.56 |
| 100% MODULUS | 3.45 | 3.26 | 3.17 | 3.16 |
| 200% MODULUS | 8.69 | 8.21 | 7.85 | 7.90 |
| 300% MODULUS | 14.2 | 13.3 | 12.9 | 13.0 |
| STRAIN@BREAK (%) | 391 | 415 | 412 | 421 |
| TOUGHNESS (MPa) | 34.3 | 36.6 | 35.0 | 36.6 |

The results for the aged samples are summarized in Table 3.

TABLE 3

| Property | Ex. 2 | Ex. 3 | Ex. 4 | Ex.5 |
|---|---|---|---|---|
| MAXIMUM STRESS | 16.1 | 17.9 | 17.2 | 17 |
| 50% MODULUS | 1.71 | 1.60 | 1.69 | 1.58 |
| 100% MODULUS | 3.66 | 3.47 | 3.55 | 3.37 |
| 200% MODULUS | 9.39 | 8.83 | 8.80 | 8.71 |
| 300% MODULUS | 15.1 | 14.1 | 14.3 | 14.3 |
| STRAIN@BREAK | 321 | 381 | 359 | 354 |
| TOUGHNESS (MPa) | 23.8 | 32.3 | 28.8 | 27.6 |
| Cycles to Failure | — | — | 221 | 22 |
| Tear Energy @ Failure | — | — | 2280 | 1660 |

Flex fatigue, sometimes referred to as fatigue to failure testing (f2f), was performed using a Monsanto™ "Fatigue to Failure" tester with a number 24 cam operating at 100 cycles per minute with modification to the test samples to accelerate testing. The test specimens were about 3 inches in length, about 0.5 inches wide at their widest width, and about 0.06 inches thick. The specimens according to ASTM D 4482 were generally dumbbell or dog bone shaped. The edges of the sample included a rib having a generally circular cross-section extending along the edge to help ensure that the sample would be adequately held within the testing device.

Various modifications and alterations that do not depart from the scope and spirit of this invention will become apparent to those skilled in the art. This invention is not to be duly limited to the illustrative embodiments set forth herein.

What is claimed is:

1. An antioxidant precursor compound represented by the formula

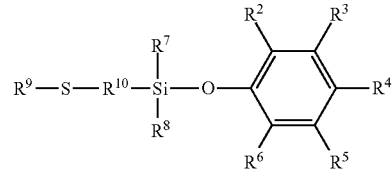

where $R^2$ through $R^6$ are each independently a hydrogen atom or a monovalent organic group, $R^7$ and $R^8$ are each independently a monovalent organic group, $R^9$ is a hydrogen atom or a blocking group, and $R^{10}$ is a covalent bond or a divalent organic group, with the proviso that at least one of $R^2$ and $R^6$ are sterically bulky groups.

2. The antioxidant precursor of claim 1, where $R^9$ is a blocking group.

3. The antioxidant precursor of claim 1, where $R^2$ is a sterically bulky group.

4. The antioxidant precursor of claim 1, where $R^2$ is a t-butyl group.

5. A vulcanizable composition of matter comprising:
(i) a vulcanizable elastomer;
(ii) a curative for the vulcanizable elastomer; and
(iii) an antioxidant precursor compound defined by the formula

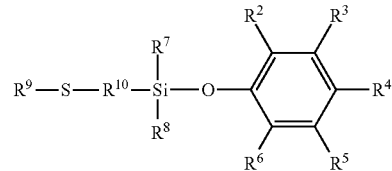

or a polymer-bound antioxidant precursor of the formula

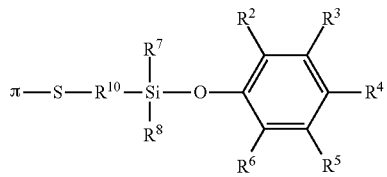

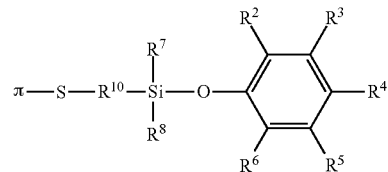

where $R^2$ through $R^6$ are each independently a hydrogen atom or a monovalent organic group, $R^7$ and $R^8$ are each independently a monovalent organic group, $R^{10}$ is a covalent bond or a divalent organic group, with the proviso that at least one of $R^2$ and $R^6$ are sterically bulky groups, $R^9$ is a hydrogen atom or a blocking group, and $\pi$ is a polymer chain or a cross-linked polymer network.

6. The vulcanizable composition of claim 5, where the vulcanizable composition further includes carbon black.

7. The vulcanizable composition of claim 5, where $R^2$ is a t-butyl group.

8. The vulcanizable composition of claim 5, where the curative is sulfur.

9. The vulcanizable composition of claim 5, where the vulcanizable elastomer is selected from the group consisting of polybutadiene, polyisoprene, poly(styrene-co-butadiene), poly(styrene-co-butadiene-co-isoprene), poly(isoprene-co-styrene), and poly(butadiene-co-isoprene), polyisoprene, poly(isobutylene-co-isoprene), polychloroprene (i.e. neoprene), poly(ethylene-co-propylene), poly(styrene-co-isoprene-co-butadiene), poly(ethylene-co-propylene-co-diene), polysulfide rubber, acrylic rubber, urethane rubber, nitrile rubber (i.e. poly(acrylonitrile-co-butadiene)), epichlorohydrin rubber, and chlorinated polyethylene.

10. A cured rubber article comprising:
a cross-linked polymer network defined by the formula where $R^2$ through $R^6$ are each independently a hydrogen atom or a monovalent organic group, $R^7$ and $R^8$ are each independently a monovalent organic group, $R^{10}$ is a covalent bond or a divalent organic group, with the proviso that at least one of $R^2$ and $R^6$ are sterically bulky groups, and $\pi$ is a polymer chain or a cross-linked polymer network.

11. The cured rubber article of claim 10, where the cured rubber article is a component of an air spring bellow.

12. The cured rubber article of claim 10, where further including carbon black.

13. The cured rubber article of claim 10, where $R^2$ is a t-butyl group.

14. The cured rubber article of claim 10, where the cured polymer network derives from the vulcanization of an elastomer selected from the group consisting of polybutadiene, polyisoprene, poly(styrene-co-butadiene), poly(styrene-co-butadiene-co-isoprene), poly(isoprene-co-styrene), and poly(butadiene-co-isoprene), polyisoprene, poly(isobutylene-co-isoprene), polychloroprene (i.e. neoprene), poly(ethylene-co-propylene), poly(styrene-co-isoprene-co-butadiene), poly(ethylene-co-propylene-co-diene), polysulfide rubber, acrylic rubber, urethane rubber, poly(acrylonitrile-co-butadiene), epichlorohydrin rubber, and chlorinated polyethylene.

15. The cured rubber article of claim 10, where the cured rubber article is a component of a tire.

* * * * *